(12) United States Patent
Schiene et al.

(10) Patent No.: US 8,618,177 B2
(45) Date of Patent: Dec. 31, 2013

(54) METHOD OF TREATING PAIN CAUSED BY INFLAMMATION

(75) Inventors: Klaus Schiene, Duesseldorf (DE); Guenter Haase, Roetgen (DE); Babette-Yvonne Koegel, Langerwehe-Hamrich (DE); Elmar Friderichs, Stolberg (DE); Ulrich Jahnel, Langerwehe (DE)

(73) Assignee: Gruenenthal GmbH, Aachen (DE)

( * ) Notice: Subject to any disclaimer, the term of this patent is extended or adjusted under 35 U.S.C. 154(b) by 37 days.

(21) Appl. No.: 12/834,655

(22) Filed: Jul. 12, 2010

(65) Prior Publication Data

US 2010/0280129 A1 Nov. 4, 2010

Related U.S. Application Data

(60) Division of application No. 11/133,190, filed on May 20, 2005, now Pat. No. 7,786,160, which is a continuation of application No. PCT/EP03/12882, filed on Nov. 18, 2003.

(30) Foreign Application Priority Data

Nov. 22, 2002 (DE) .................................. 102 54 785
Jun. 6, 2003 (DE) .................................. 103 26 103

(51) Int. Cl.
*A61K 31/137* (2006.01)

(52) U.S. Cl.
USPC ....................................................... 514/654

(58) Field of Classification Search
USPC .................. 514/650, 406, 646, 506, 445, 654
See application file for complete search history.

(56) References Cited

U.S. PATENT DOCUMENTS

| | | | |
|---|---|---|---|
| 4,389,393 A | 6/1983 | Schor et al. | |
| 5,330,761 A | 7/1994 | Baichwal | |
| 5,399,362 A | 3/1995 | Baichwal et al. | |
| 5,455,046 A | 10/1995 | Baichwal | |
| 5,472,711 A | 12/1995 | Baichwal | |
| 5,516,803 A | 5/1996 | Raffa | |
| 5,733,936 A | 3/1998 | Buschmann et al. | |
| 6,248,737 B1 * | 6/2001 | Buschmann et al. | 514/231.8 |
| 6,344,558 B1 | 2/2002 | Buschmann et al. | |
| 6,673,794 B2 | 1/2004 | Puetz et al. | |
| 6,908,944 B2 | 6/2005 | Christoph et al. | |
| 7,022,739 B2 | 4/2006 | Buschmann et al. | |
| 7,168,937 B2 | 1/2007 | Buschmann et al. | |
| RE39,593 E | 4/2007 | Buschmann et al. | |
| 7,786,160 B2 | 8/2010 | Schiene et al. | |
| 2002/0010178 A1 | 1/2002 | Buschmann et al. | |
| 2002/0132825 A1 | 9/2002 | Burch et al. | |
| 2003/0220389 A1 | 11/2003 | Buschmann et al. | |
| 2004/0034105 A1 | 2/2004 | Christoph et al. | |
| 2012/0034304 A1 | 2/2012 | Bartholomaeus et al. | |

FOREIGN PATENT DOCUMENTS

| | | |
|---|---|---|
| DE | 33 09 516 A1 | 12/1983 |
| DE | 44 26 245 A | 2/1996 |
| DE | 195 25 137 A | 1/1997 |
| DE | 100 59 412 A1 | 6/2002 |
| EP | 0 693 475 A1 | 1/1996 |
| EP | 1 219 594 | 7/2002 |
| WO | WO 00 51685 | 9/2000 |
| WO | WO 01 49654 | 7/2001 |
| WO | WO 01/57232 A1 | 8/2001 |
| WO | WO 02/26694 A1 | 4/2002 |
| WO | WO 02 28817 | 4/2002 |
| WO | WO 02/067651 A2 | 9/2002 |
| WO | WO 03/035053 A1 | 5/2003 |
| WO | WO 03/103650 A1 | 12/2003 |
| WO | WO 03/105808 A1 | 12/2003 |

OTHER PUBLICATIONS

K. Schiene et al., Antinociceptive and Antihyperalgesic Effects of Tapentadol in Animal Models of Inflammatory Pain, The Journal of Pharmacology and Experimental Therapeutics, vol. 339, No. 2, pp. 537-544, (2011).
T. Issiouri et al., "The Efficacy of Premedication with Celecoxib and Acetaminophen in Preventing Pain After Otolaryngologic Surgery", Anesth. Analg., May 2002, p. 1188, vol. 94.
Raymond Sinatra, MD, PhD, "Role of COX-2 Inhibitors in the Evolution of Acute Pain Management", Journal of Pain and Symptom Management, Jul. 15, 2002, pp. S18-S27, vol. 24, No. 15, US Cancer Pain Relief Committee, Elsevier, New York, New York, USA.
German Office Action dated Oct. 23, 2003.
Souillac et al., Characterization of delivery systems, differential scanning calorimetry, pp. 217-218 (in Encyclopedia of Controlled Drug Delivery, 1991, John Wiley & Sons, pp. 212-227).
Vippagunta et al., Advanced Drug Delivery Reviews, 48 (2001), pp. 3-26.
P.S.V. Satyanarayana et al., Isobolographic analysis of interaction between cyclooxygenase inhibitors and tramadol in acetic acid-induced writhing in mice, Progress in Neuro-Psychopharmacology & Biological Psychiatry 28 (2004) pp. 641-649.
Tapentadol Hydrochloride, Drugs of the Future 2006, 31(12), pp. 1053-1061.
Pschyrembel, Klinisches Wörterbuch, 256. ed., 1990, Walter de Gruyter, pp. 1501-1502, keyword "Schmerzsyndrome" (pain sundromes) with translation (six(6) pages).
L.C. Hendershot et al., "Antagonism of the Frequency of Phenylquinone Induced Writhing in the Mouse by Weak Analgesics and Nonanalgesics," J. Pharmcol. Exptl. Ther., vol. 125, 237-240 (1959) (four (4) pages).

(Continued)

*Primary Examiner* — Jennifer M Kim
(74) *Attorney, Agent, or Firm* — Crowell & Moring LLP

(57) ABSTRACT

A method of treating or inhibiting, in particular, pain caused by inflammation in a mammal by administering to the mammal an effective inflammatory pain alleviating amount of a (1R,2R)-3-(3-dimethylamino-1-ethyl-2-methyl-propyl)-phenol compound or a physiologically acceptable salt thereof, such as the hydrochloride or citrate salt.

7 Claims, 2 Drawing Sheets

(56) References Cited

OTHER PUBLICATIONS

International Search Report dated Mar. 15, 2004 (five (5) pages).
Fendrich, Selective COX-2 inhibitor meloxicam: Survey of pharmacological properties and clinical experiences. Prakticky Lekar, 1999 vol. 79 No. 1 pp. 36-40. ISSN: 0032-6739, abstract. (one (1) page).
Le Bars, D. et al., "Animal Models of Nociception," Pharmacol Rev., 53:597-652, 2001. (fifty-six (56) pages).
Abstract of Bannon, A.W. and Malmberg A.B., "Models of Nociception: Hot-Plate, Tail-Flick, and Formalin Tests in Rodents," Curr. Prot. Neurosci., 41:8.9.1-8.9.16 (2007). (one (1) page).
Negus, SS., Vanderah, T.W., Brandt, M.R., Bilsky, E.J., Becerra, L., Borsook, D., "Preclinical assessment of candidate analgesic drugs: recent advances and future challenges," Review, J. Pharmacol. Exp. Ther., Nov; 319(2):507-14 (2006) [E-published Jun. 2, 2006] (eight (8) pages).
Huidobro, F., Huidobro-Toro, J.P., Leong, Way E., "Studies on tolerance development to single doses of morphine in mice," J. Pharmacol. Exp. Ther., Aug. 198(2):318-29 (1976) (twelve (12) pages).
D'Amour, F.E. and Smith, D.L., "A method for determining loss of pain sensation," J. Pharmacol. Exp. Ther., 72:74-78 (1941) (six (6) pages).
Randall, L.O. and Selitto, J.J., "A method for measurement of analgesic activity on inflamed tissue," Arch. Int. Pharmacodyn. Ther. Sep., 1111(4):409-19 (1957) (eleven (11) pages).
International Preliminary Examination Report dated Apr. 19, 2005 (twenty-six (26) pages).
Translation of International Preliminary Examination Report dated Apr. 19, 2005 (seven (7) pages).
File history of European patent application No. 07 014 417.5 (granted as European patent No. 1 839 654 B9) dated Feb. 20, 2013-Apr. 29, 2013 (ninety-nine (99) pges).
File history of European patent application No. 07 014 417.5 (granted as European patent No. 1 839 654 B9) dated Jul. 23, 2007-Dec. 21, 2012 (five hundred fifty-one (551) pages).
European Search Report in European patent application No. 07 014 417.5 (granted as European patent No. 1 839 654 B9) dated Sep. 20, 2007 (five (5) pages).
Schiene et al., "Antinociceptive and Antihyperalgesic Effects of Tapentadol in Animal Models of Inflammatory Pain," *Journal of Pharmacology and Experimental Therapeutics*, 2011, 339(2):537-544 (eight (8) pages).
Eckhardt et al., "Etiology of Chemically Induced Writhing in Mouse and Rat," *Exp Biol Med (Maywood)* 1958 98: 186-188 (four (4) sheets).
Ravin, L. PhD., "Preformulation", Remington Chapter 76, pp. 1409-1423, 1985 (fifteen (15) sheets).
Disanto, A., "Bioavailability and Bioequivalency Testing", Remington Chapter 77, pp. 1424-1431, 1985 (eight (8) sheets).
Knevel, A. PhD., "Separation", Remington Chapter 78, pp. 1432-1442, 1985 (eleven (11) sheets).
Phillips, G Briggs, PhD., "Sterilization", Remington Chapter 79, pp. 1443-1454, 1985 (twelve (12) sheets).
Siegel, F. PhD., "Tonicity, Osmoticity, Osmolality and Osmolarity", Remington Chapter 80, pp. 1455-1472, 1985 (eighteen (18) sheets).
Giles et al., "Plastic Packaging Materials", Remington Chapter 81, pp. 1473-1477, 1985 (five (5) sheets).
Lintner, C. PhD., "Stability of Pharmaceutical Products", Remington Chapter 82, pp. 1478-1486, 1985 (nine (9) sheets).
Erskine, C., Jr., "Quality Assurance and Control" Remington Chapter 83, pp. 1487-1491, 1985 (five (5) sheets).
Nairn, J.G. PhD., "Solutions, Emulsions, Suspensions and Extractives", Remington Chapter 84, pp. 1492-1517, 1985 (twenty-six (26) sheets).
Avis, K. DSc., "Parenteral Preparations", Remington Chapter 85, pp. 1518-1541, 1985 (twenty-four (24) sheets).
Turco et al., "Intravenous Admixtures", Remington Chapter 86, pp. 1542-1552, 1985 (eleven (11) sheets).
Mullins, J. PhD., "Ophthalmic Preparations", Remington Chapter 87, pp. 1553-1566, 1985 (fourteen (14) sheets).
Block, L. PhD., "Medicated Applications", Remington Chapter 88, pp. 1567-1584, 1985 (eighteen (18) sheets).
Rippie, E. PhD., "Powders", Remington Chapter 89, pp. 1585-1602 (eighteen, 1985 (18) sheets).
King et al., "Oral Solid Dosage Forms", Remington Chapter 90, pp. 1603-1632, 1985 (thirty (30) sheets).
Porter, S. PhD., "Coating of Pharmaceutical Dosage Forms", Remington Chapter 91, pp. 1633-1643, 1985 (eleven (11) sheets).
Longer et al., "Sustained-Release Drug Delivery Systems", Remington Chapter 92, pp. 1644-1661, 1985 (eighteen (18) sheets).
Sclarra et al., "Aerosols", Remington Chapter 93, 1985, pp. 1662-1677, 1985 (sixteen (16) sheets).
Buschmann et al., "Analgesics, From Chemistry and Pharmacology to Clinical Application"; (eds.), 1st edition, Wiley-VCH, pp. 13-126. 2002 (Cover Page (fifty-eight (58) pages).
Dubuisson et al., "The Formalin Test: A Quantitative Study of the Analgesic Effects of Morphine, Meperidine, and Brain Stem Stimulation in Rats and Cats", Pain, vol. 4, pp. 161-174, 1977 (fourteen (14) pages).

* cited by examiner

METHOD OF TREATING PAIN CAUSED BY INFLAMMATION

CROSS REFERENCE TO RELATED APPLICATIONS

This application is a division of application Ser. No. 11/133,190, filed May 20, 2005, now U.S. Pat. No. 7,786,160, which in turn is a continuation of International Patent Application No. PCT/EP2003/012882, filed Nov. 18, 2003, designating the United States of America, and published in German as WO 2004/047823, the entire disclosure of which is incorporated herein by reference. Priority is claimed based on German Patent Application Nos. 102 54 785.8, filed Nov. 22, 2002, and 103 26 103.6, filed Jun. 6, 2003.

FIELD OF THE INVENTION

The present invention relates to a method of treating or inhibiting pain, particularly pain caused by inflammation or inflammatory pain.

BACKGROUND OF THE INVENTION

The treatment of chronic and non-chronic pain conditions is extremely important in medicine. There is currently a worldwide demand for additional, not exclusively opioid-based, but highly effective, pain treatment. The urgent need for action for patient-oriented and purposeful treatment of chronic and non-chronic pain conditions, this being taken to mean the successful and satisfactory treatment of pain for the patient, is documented in the large number of scientific papers which have recently appeared in the field of applied analgesics and fundamental research work on nociception.

Even if the analgesics that are conventionally used for treating pain, for example opioids, NA- and 5HT-reuptake inhibitors, NSAIDS and also COX inhibitors, are analgesically effective, side effects nevertheless sometimes occur, in particular in the case of the more active opioids.

SUMMARY OF THE INVENTION

The object of the present invention is therefore to provide new methods for treating, in particular, inflammatory pain or pain due to inflammation.

It has been found that (1R,2R)-3-(3-dimethylamino-1-ethyl-2-methyl-propyl)-phenol or a physiologically acceptable salt thereof is unexpectedly particularly effective in treating or inhibiting inflammatory pain.

Accordingly, the invention relates to a method of treating or inhibiting inflammatory pain in a mammal in need thereof, comprising administering to said mammal a pharmacologically effective amount of (1R,2R)-3-(3-dimethylamino-1-ethyl-2-methyl-propyl)-phenol or a physiologically acceptable salt thereof. Particularly preferred physiologically acceptable salts are the hydrochloride salt and the citrate salt. The active substance may also be administered in the form of a solvate, particularly a hydrate.

The active substance is advantageously administered in the form of a substantially pure stereoisomer, in particular, enantiomer or diastereomer, or in the form of a mixture of the stereoisomers containing predominantly the 1R,2R enantiomers or diastereomers.

The active substance 3-(3-dimethylamino-1-ethyl-2-methyl-propyl)-phenol corresponds to a compound of the following formula I:

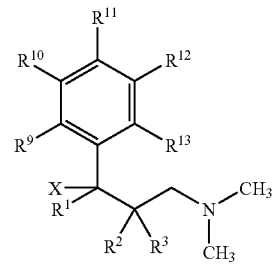

in which
X is H;
$R^1$ is ethyl;
$R^2$ is methyl;
$R^3$ is H;
$R^9$, $R^{11}$ and $R^{13}$ are each H; and
one of $R^{10}$ and $R^{12}$ is OH, while the other is H.

The active substance is advantageously administered in the form of a substantially pure stereoisomer, in particular, enantiomer or diastereomer, or in the form of a mixture of the stereoisomers containing predominantly the 1R,2R enantiomers or diastereomers.

In the context of this invention, alkyl and cycloalkyl radicals are taken to mean saturated and unsaturated (but not aromatic), branched, unbranched and cyclic hydrocarbons which may be unsubstituted or singly or multiply substituted. In this case $C_{1-2}$ alkyl represents C1 or C2 alkyl, $C_{1-3}$ alkyl represents C1, C2 or C3 alkyl, $C_{1-4}$ alkyl represents C1, C2, C3 or C4 alkyl, $C_{1-5}$ alkyl represents C1, C2, C3, C4 or C5 alkyl, $C_{1-6}$ alkyl represents C1, C2, C3, C4, C5 or C6 alkyl, $C_{1-7}$ alkyl represents C1, C2, C3, C4, C5, C6 or C7 alkyl, $C_{1-8}$ alkyl represents C1, C2, C3, C4, C5, C6, C7 or C8 alkyl, $C_{1-10}$ alkyl represents C1, C2, C3, C4, C5, C6, C7, C8, C9 or C10 alkyl and $C_{1-18}$ alkyl represents C1, C2, C3, C4, C5, C6, C7, C8, C9, C10, C11, C12, C13, C14, C15, C16, C17 or C18 alkyl. Furthermore $C_{3-4}$ cycloalkyl represents C3 or C4 cycloalkyl, $C_{3-5}$ cycloalkyl represents C3, C4 or C5 cycloalkyl, $C_{3-6}$ cycloalkyl represents C3, C4, C5 or C6 cycloalkyl, $C_{3-7}$ cycloalkyl represents C3, C4, C5 or C7 cycloalkyl, $C_{3-8}$ cycloalkyl represents C3, C4, C5, C6, C7 or C8 cycloalkyl, $C_{4-5}$ cycloalkyl represents C4 or C5 cycloalkyl, $C_{4-6}$ cycloalkyl represents C4, C5 or C6 cycloalkyl, $C_{4-7}$ cycloalkyl represents C4, C5, C6 or C7 cycloalkyl, $C_{5-6}$ cycloalkyl represents C5 or C6 cycloalkyl and $C_{5-7}$ cycloalkyl represents C5, C6 or C7 cycloalkyl. With respect to cycloalkyl, the term also comprises saturated cycloalkyls, in which one or two carbon atoms are replaced by a heteroatom, S, N or O. However, the term cycloalkyl also includes singly or multiply, preferably singly, unsaturated cycloalkyls without a heteroatom in the ring, if the cycloalkyl is not an aromatic system. The alkyl and cycloalkyl radicals are preferably methyl, ethyl, vinyl (ethenyl), propyl, allyl (2-propenyl), 1-propinyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, cyclopropyl, 2-methylclopropyl, cyclopropylmethyl, cyclobutyl, cyclopentyl, cyclopentylmethyl, cyclohexyl, cycloheptyl, cyclooctyl, but also adamantyl, $CHF_2$, $CF_3$ or $CH_2OH$ and pyrazolinone, oxopyrazolinone, [1,4]dioxan or dioxolan.

In this case, in conjunction with alkyl and cycloalkyl—unless this is not explicitly defined otherwise—the term substituted in the context of this invention denotes the substitution of at least one (optionally also more) hydrogen radical(s) for F, Cl, Br, I, $NH_2$, SH, $OCH_3$, $SCH_3$, $N(CH_3)_2$, $NHCH_3$ or OH, wherein "multiply substituted" or "substituted" with multiple substitution denotes that the substitution is made both on different and on the same atoms multiply with the same or different substituents, for example threefold on the same carbon atom as in the case of $CF_3$ or at different points as in the case of —CH(OH)—CH=CH—$CHCl_2$. Particularly preferred substituents in this case are F, Cl and OH. With respect to cycloalkyl, the hydrogen radical can also be replaced by $OC_{1-3}$ alkyl or $C_{1-3}$ alkyl (singly or multiply substituted or unsubstituted respectively), in particular methyl, ethyl, n-propyl, i-propyl, $CF_3$, methoxy or ethoxy.

The term $(CH_2)_{3-6}$ is taken to mean —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and $CH_2$—$CH_2$—$CH_2$—$CH_2$—$CH_2$—$CH_2$—, $(CH_2)_{1-4}$ to mean —$CH_2$—, —$CH_2$—$CH_2$—, —$CH_2$—$CH_2$—$CH_2$— and —$CH_2$—$CH_2$—$CH_2$—$CH_2$—, $(CH_2)_{4-5}$ to mean —$CH_2$—$CH_2$—$CH_2$—$CH_2$— and —$CH_2$—$CH_2$—$CH_2$—$CH_2$—$CH_2$—, etc.

An aryl radical denotes ring systems with at least one aromatic ring but without heteroatoms even in only one of the rings. Examples are phenyl, naphthyl, fluoroanthenyl, fluorenyl, tetralinyl or indanyl, which can be unsubstituted or singly or multiply substituted.

A heteroaryl radical denotes heterocyclic ring systems with at least one unsaturated ring, which contain one or more heteroatoms from the group comprising nitrogen, oxygen and/or sulphur and which can also be singly or multiply substituted. Examples of suitable heteroaryl groups include furan, benzofuran, thiophene, benzothiophene, pyrrole, pyridine, pyrimidine, pyrazine, quinoline, isoquinoline, phthalazine, benzo[1,2,5]thiadiazole, benzothiazole, indole, benzotriazole, benzodioxolan, benzodioxan, carbazole, indole and quinazoline.

In this case, in conjunction with aryl and heteroaryl, substituted denotes the substitution of the aryl or heteroaryl by $R^{22}$, $OR^{22}$, a halogen, preferably F and/or Cl, a $CF_3$, a CN, a $NO_2$, a $NR^{23}R^{24}$, a $C_{1-6}$ alkyl (saturated), a $C_{1-6}$ alkoxy, a $C_{3-8}$ cycloalkoxy, a $C_{3-8}$ cycloalkyl or a $C_{2-6}$ alkylene. In this case the radical $R^{22}$ represents H, a $C_{1-10}$ alkyl, preferably a $C_{1-6}$ alkyl, an aryl or heteroaryl radical or an aryl or heteroaryl radical bound by $C_{1-3}$ alkyl, saturated or unsaturated, or a $C_{1-3}$ alkylene-group-bound aryl or heteroaryl radical, wherein these aryl or heteroaryl radicals must not themselves be substituted by aryl or heteroaryl radicals. The radicals $R^{23}$ and $R^{24}$, which may be the same or different, represent H, a $C_{1-10}$ alkyl, preferably a $C_{1-6}$ alkyl, an aryl radical, a heteroaryl radical or an aryl or heteroaryl radical bound by saturated or unsaturated $C_{1-3}$ alkyl or a $C_{1-3}$ alkylene-group-bound aryl or heteroaryl radical, wherein these aryl or heteroaryl radicals must not themselves be substituted by aryl or heteroaryl radicals. Alternatively, the radicals $R^{23}$ and $R^{24}$ together mean $CH_2CH_2OCH_2CH_2$, $CH_2CH_2NR^{25}CH_2CH_2$ or $(CH_2)_{3-6}$. The radical $R^{25}$ represents H, a $C_{1-10}$ alkyl, preferably a $C_{1-6}$ alkyl, an aryl radical, a heteroaryl radical or an aryl or heteroaryl radical bound by saturated or unsaturated $C_{1-3}$ alkyl or a $C_{1-3}$ alkylene-group-bound aryl or heteroaryl radical, wherein these aryl or heteroaryl radicals must not themselves be substituted by aryl or heteroaryl radicals.

The term "salt" denotes any form of the active ingredient according to the invention in which it assumes or is charged with an ionic form and is coupled to a counter ion (a cation or anion) or is in solution. This also includes complexes of the active ingredient with other molecules and ions, in particular complexes which are complexed by ion interaction. In particular this is taken to mean (and this is also a preferred embodiment of this invention) physiologically acceptable salts, in particular physiologically acceptable salts with cations or bases and physiologically acceptable salts with anions or acids or even a salt formed with a physiologically acceptable acid or physiologically acceptable cation.

The "term physiologically acceptable salt with anions or acids" denotes, in the context of this invention, salts of at least one of the compounds according to the invention—usually protonated, for example on nitrogen—as a cation with at least one anion which are physiologically acceptable—in particular when administered to humans and/or mammals. In the context of this invention this denotes, in particular, the salt formed with a physiologically acceptable acid, namely salts of the respective active ingredient with inorganic or organic acids, which are physiologically acceptable—in particular when administered to humans and/or mammals. Examples of physiologically acceptable salts of specific acids are salts of: hydrochloric acid, hydrobromic acid, sulphuric acid, methane sulphonic acid, formic acid, acetic acid, oxalic acid, succinic acid, malic acid, tartaric acid, mandelic acid, fumaric acid, lactic acid, citric acid, glutamic acid, 1,1-dioxo-1,2-dihydro1b6-benzo[d]isothiazol-3-one (saccharic acid), monomethyl sebacic acid, 5-oxo-proline, hexane-1-sulphonic acid, nicotinic acid, 2-, 3- or 4-amino benzoic acid, 2,4,6-trimethyl-benzoic acid, α-lipoic acid, acetyl glycine, acetylsalicylic acid, hippuric acid and/or aspartic acid. Hydrochloride salt and citrate are particularly preferred.

The term "salt formed with a physiologically acceptable acid", in the context of this invention, is taken to mean salts of the respective active ingredient with inorganic or organic acids which are physiologically acceptable—in particular when administered to humans and/or mammals. Hydrochloride and citrate are particularly preferred. Examples of physiologically acceptable acids include: hydrochloric acid, hydrobromic acid, sulphuric acid, methane sulphonic acid, formic acid, acetic acid, oxalic acid, succinic acid, tartaric acid, mandelic acid, fumaric acid, lactic acid, citric acid, glutamic acid, 1,1-dioxo-1,2-dihydro1λ$^6$-benzo[d]isothiazol-3-one (saccharic acid), monomethyl sebacic acid, 5-oxo-proline, hexane-1-sulphonic acid, nicotinic acid, 2-, 3- or 4-amino benzoic acid, 2,4,6-trimethyl-benzoic acid, α-lipoic acid, acetyl glycine, acetylsalicylic acid, hippuric acid and/or aspartic acid.

The term "physiologically acceptable salt with cations or bases" denotes, in the context of this invention, salts of at least one of the compounds according to the invention—usually a (deprotonated) acid—as an anion with at least one, preferably inorganic, cation, which are physiologically acceptable, in particular when administered to humans and/or mammals. The salts of the alkali and alkaline-earth metals are particularly preferred, but also $NH_4^+$, in particular however (mono) or (di) sodium, (mono) or (di) potassium, magnesium or calcium salts.

The term "salt formed with a physiologically acceptable cation" is taken to mean, in the context of this invention, salts of at least one of the respective compounds as an anion with at least one inorganic cation, which are physiologically acceptable, in particular when administered to humans and/or mammals. The salts of the alkali and alkaline-earth metals are particularly preferred, but also $NH_4^+$, in particular however (mono) or (di) sodium, (mono) or (di) potassium, magnesium or calcium salts.

Substituted 1-phenyl-3-dialkylamino-propane compounds and the production thereof are known from U.S. Pat. No. 6,248,737 (=DE 44 26 245).

The term "COX-II inhibitors" refers to selective inhibitors of COX II, the inducible isoform of cyclooxygenase.

Cyclooxygenase is a synonym for prostaglandin endoperoxide synthase; an enzyme that combines the function of a dioxgenase and a peroxidase and, as a key enzyme, catalyses the conversion of arachidonic acid into prostaglandin H2 or peroxides (see Walter de Gruyter, Pschyrembel, 258$^{th}$ edition; Roche Lexikon Medizin, 4$^{th}$ edition). Further information regarding COX-II inhibitors, in particular listings thereof, may be found on pp. 13 to 126 and in particular 21 to 31 of "Analgesics, From Chemistry and Pharmacology to Clinical Application"; Buschmann et al (eds.), 1$^{st}$ edition, Wiley-VCH, 2002. All of the content of this chapter is part of the description of this invention. The term "COX-II inhibitors" refers in particular, by way of example, to Celecoxib, Rofecoxib, Etoricoxib, Valdecoxib, Parecoxib, Etodolac, Meloxicam or Nimesulide. Celecoxib, which is sold under the name LOSEC® or Prilosec® or CELEBREX®, and Rofecoxib, which is sold under the name VIOXX®, are of particular importance. The term "selectively correspondingly preferred" denotes that the compound displays more pronounced inhibition of COX II than of COX I and/or in particular exhibits an $IC_{50}$ that is ≥5 lower on COX II than on COX 1.

In particular, the 3-(3-dimethylamino-1-ethyl-2-methyl-propyl)-phenol compound of the invention in which $R^3$=H is in the form of the 1R,2R diastereomer having the relative configuration Ia

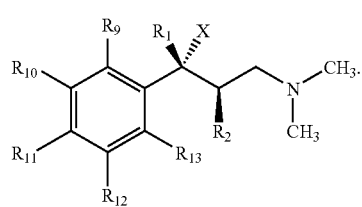

Ia

In particular in mixtures which have a relatively high content of this diastereomer in comparison to the other diastereomer are used, or a substantially pure diastereomer is used. In particular the compound (−)-(1R,2R)-3-(3-dimethylamino-1-ethyl-2-methyl-propyl)-phenol is used, preferably as the hydrochloride or as the citrate.

In one preferred embodiment, the 3-(3-dimethylamino-1-ethyl-2-methyl-proply)-phenol compound according to the invention may be used in combination with a COX-II inhibitor. Particularly preferred COX-II inhibitors may be selected from the group consisting of Celecoxib, Rofecoxib, Etoricoxib, Valdecoxib, Parecoxib, Etodolac, Meloxicam and Nimesulide, especially particularly preferably Celecoxib or Rofecoxib.

The active ingredients according to the invention are toxicologically safe, so the invention also relates to a pharmaceutical composition containing an active ingredient combination according to the invention; and optionally suitable additives and/or auxiliaries or active ingredients;

Suitable additives and/or auxiliaries, in the context of this invention, are any substances known to a person skilled in the art from the prior art for obtaining galenical formulations. The choice of these auxiliaries and the amounts thereof to be used depend on whether the pharmaceutical preparation is to be administered orally, intravenously, intraperitoneally, intradermally, intramuscularly, intranasally, buccally, rectally or topically. Preparations in the form of tablets, chewing tablets, dragees, capsules, granules, drops, juices or syrups are suitable for oral administration, solutions, suspensions, easily reconstitutable dry preparations and sprays are suitable for parenteral, topical and inhalative administration. Suppositories for rectal administration are a further possibility. Administration in a deposit, in dissolved form, in a carrier foil or a plaster, optionally with the addition of agents to promote skin penetration, are examples of suitable percutaneous administration preparations. Examples of auxiliaries and additives for oral administration preparations include blasting agents, lubricants, binders, fillers, mould release agents, optionally solvents, flavouring agents, sugar, in particular carrier agents, diluents, dyes, antioxidants, etc. Waxes and fatty acid esters may, inter alia, be used as suppositories and carrier substances, preservatives and suspension auxiliaries, etc. may be used as parenteral administration agents. The amount of active ingredient to be administered to the patient varies as a function of the weight of the patient, the method of administration and the severity of the illness. The compounds according to the invention may be released after a delay from preparations that may be administered orally, rectally or percutaneously. In the indication according to the invention, suitable retarding formulations, in the form of a "once-daily" preparation that only has to be taken once a day, are particularly preferred.

Also preferred are pharmaceutical compositions containing at least 0.05 to 90.0% of the active ingredient, in particular low effective doses, in order to prevent side effects or analgesic effects. Conventionally, 0.1 to 5000 mg of the combination per kg of body weight, in particular 1 to 500 mg per kg, preferably 2 to 250 mg per kg are administered. Also preferred and conventional, however, is the administration of 0.01 to 5 mg/kg, preferably 0.03 to 2 mg/kg, in particular 0.05 to 1 mg/kg of body weight.

Examples of suitable auxiliaries may include: water, ethanol, 2-propanol, glycerol, ethylene glycol, propylene glycol, polyethylene glycol, polypropylene glycol, glucose, fructose, lactose, saccharose, dextrose, molasses, starch, modified starch, gelatine, sorbitol, inositol, mannitol, microcrystalline cellulose, methyl cellulose, carboxymethyl cellulose, cellulose acetate, shellac, cetyl alcohol, polyvinyl pyrrolidone, paraffins, waxes, natural and synthetic gums, acacia gum, alginates, dextran, saturated and unsaturated fatty acids, stearic acid, magnesium stearate, zinc stearate, glycerol stearate, sodium lauryl sulphate, edible oils, sesame oil, coconut oil, peanut oil, soybean oil, lecithin, sodium lactate, polyoxyethylene and polypropylene fatty acid ester, sorbitan fatty acid ester, sorbic acid, benzoic acid, citric acid, ascorbic acid, tannic acid, sodium chloride, potassium chloride, magnesium chloride, calcium chloride, magnesium oxide, zinc oxide, silicon dioxide, titanium oxide, titanium dioxide, magnesium sulphate, zinc sulphate, calcium sulphate, potash, calcium phosphate, dicalcium phosphate, potassium bromide, potassium iodide, talcum, kaolin, pectin, Crospovidon, agar and bentonite.

The pharmaceutical compositions according to the invention are produced using means, devices, methods and processes that are well known in the prior art of pharmaceutical formulations, as described for example in "Remington's Pharmaceutical Sciences", A. R. Gennaro (ed.), 17$^{th}$ edition, Mack Publishing Company, Easton, Pa. (1985), in particular in part 8, chapters 76 to 93.

Thus, for a solid formulation, such as a tablet, for example, the active ingredient of the pharmaceutical composition may be granulated with a pharmaceutical carrier, for example conventional tablet ingredients such as corn starch, lactose, saccharose, sorbitol, talcum, magnesium stearate, dicalcium phosphate or pharmaceutically acceptable gums, and pharmaceutical diluents, for example water, in order to form a solid composition that contains an active ingredient in homogeneous distribution. The term "homogeneous distribution" is taken to mean that the active ingredient is distributed uniformly over the entire composition, so that said composition may easily be divided into equally effective unit dose forms, such as tablets, pills or capsules. The solid composition is then divided into unit dose forms. The tablets or pills of the pharmaceutical composition according to the invention or of the compositions according to the invention may also be coated or compounded in a different manner, in order to provide a dose form with a delayed release. Suitable coating agents include polymer acids and mixtures of polymer acids with materials such as shellac, cetyl alcohol and/or cellulose acetate.

The invention also relates to a method for the treatment of pain in which the active ingredient according to the invention is used.

A further preferred subject of the invention is a therapy, in particular a therapy regimen, in which, in order to treat pain, a COX-II inhibitor is given before giving the analgesic 3-(3-dimethylamino-1-ethyl-2-methyl-proply)-phenol compound, as this has proven to be particularly advantageous. Particularly preferably, the COX-II inhibitor is given at least 30 minutes, preferably 1 hour before giving the 3-(3-dimethylamino-1-ethyl-2-methyl-proply)-phenol compound. This may be done, for example, directly by the relevant doctor, but also (for example, on the doctor's instructions) by the patient himself. The active ingredient combination may also be separated into various pharmaceutical preparations, and may in particular also be in the form of various pharmaceutical packages. A possible and also advantageous embodiment of this invention would be a kit in which the active ingredients of the active ingredient combination according to the invention, although spatially separated, are provided in a presentation form, for example a pharmaceutical composition package. A "kit" of this type is accordingly also a preferred embodiment of the invention.

EXAMPLES

The following examples are intended to illustrate and clarify certain embodiments of the invention, however they are not intended to and should not be understood to limit the subject matter of the invention.

Figure 1:
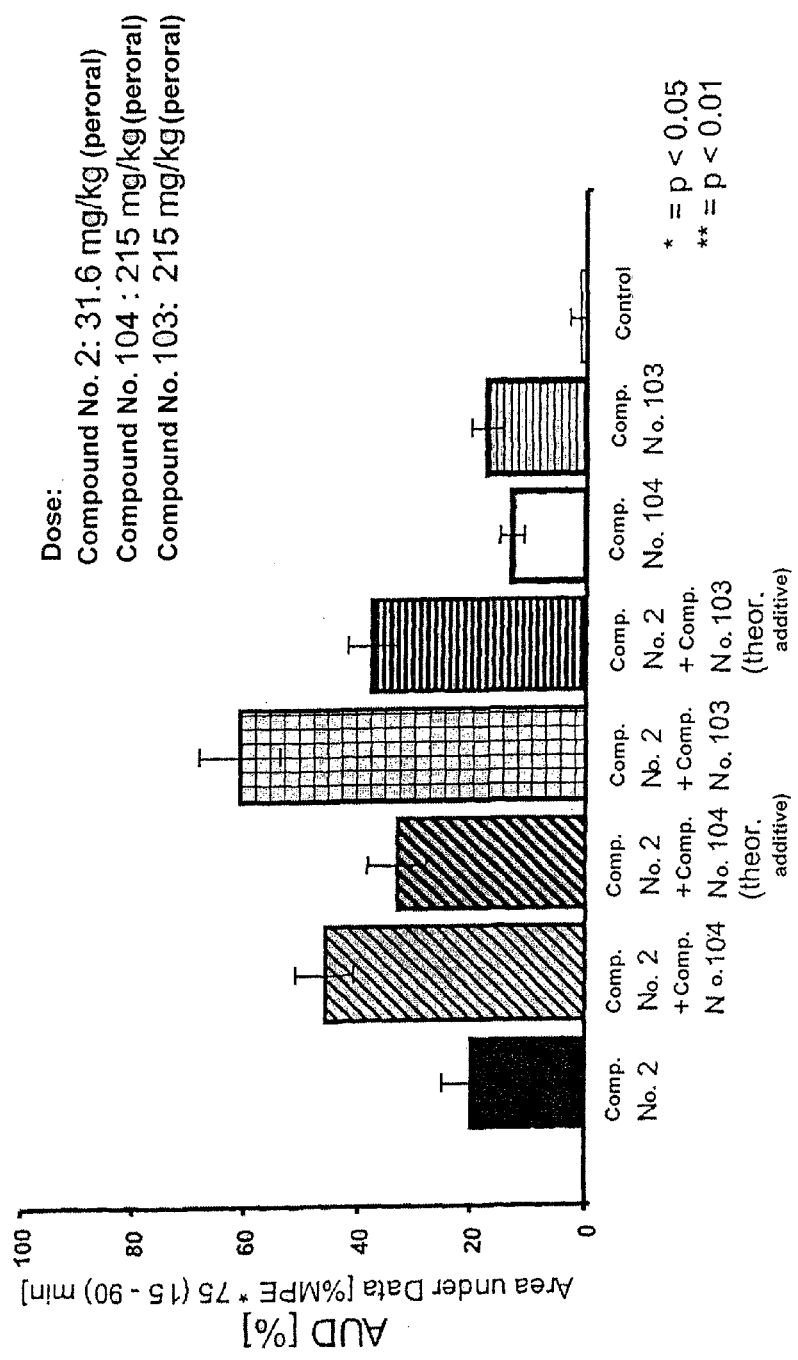
FIGS. 1 and 2 are bar graphs showing the effect of two different dosages of (1R,2R)-3-(3-dimethylamino-1-ethyl-2-methyl-propyl)-phenol in the Randall-Selitto test, as well as the effects of individual administrations of the COX-II inhibitors, the expected additive effects of administrations of (1R,2R)-3-(3-dimethylamino-1-ethyl-2-methyl-propyl)-phenol and the COX-II inhibitors, and the surprising supra-additive effects achieved by the combination of (1R,2R)-3-(3-dimethylamino-1-ethyl-2-methyl-propyl)-phenol and the COX-II inhibitors in the Randall-Selitto test described below, in the case of staggered administration. The COX inhibitors (compound 104 or 103) were administered perorally to rats 1 hour before the administration of the (1R,2R)-3-(3-dimethylamino-1-ethyl-2-methyl-propyl)-phenol compound.

AUD=area under data.

% MPE=% of the maximum possible effect, wherein the maximum possible effect=100%.

EXAMPLE 1

Effects in the Randall-Selitto Test

The compounds, which were tested with regard to their efficacy, are listed below. The numbering is used in the examples and the figures:

Test Compound: (compound no. 2)
(1R,2R)-3-(3-dimethylamino-1-ethyl-2-methyl-propyl)-phenol, hydrochloride
COX II-Inhibitors:

| Name | Compound No. |
|---|---|
| Celecoxib | 101 |
| Rofecoxib | 102 |
| Celecoxib in the form of the final pharmaceutical composition CELEBREX ® | 103 |
| Rofecoxib in the form of the final pharmaceutical composition VIOXX ® | 104 |

EXAMPLE 2

Writhing Test on Mouse

The writhing test is a modification of the method of Schmauss C and Yaksh T L, J Pharmacol Exp Ther 228: 1-12 (1984) and a model for acute pain.

9% acetic acid was administered to the animals intraperitoneally as a pain stimulus. This was administered 30 min (test substance perorally) or 10 min (test substance intravenously) after the administration of the test substance. The pain-induced writhing reactions were recorded 10 to 35 min after the administration of acetic acid. As rats rarely exhibit the conventional writhing reaction of mice, but do exhibit other very clear expressions of pain, the evaluation took place on the basis of a score division. Pain expressions, such as a slanting body angle when the animal stands upright, frequent cleaning of the belly or arching of the back without stretching of the rear limbs, were thus included in the evaluation.

The animals that had been treated with the substance were compared with a control group, which had been given physiological saline solution. The group contained 10 animals (n=10).

The result of the administration of compound no 2 as well as the result of administrations of the active ingredient combination of compound no. 2 with the COX-II inhibitors 101, 102, 103 and 104 can be seen from Table 1.

EXAMPLE 3

Formalin Test

The formalin test (Dubuisson, D. and Dennis, S. G., 1977, Pain, 4, 161 to 174) is a model for acute and chronic pain. In the tests presented here, the chronic pain component was evaluated.

By means of a single formalin injection into the dorsal side of a hind paw of test animals that were able to move freely, a biphasic nociceptive reaction, which was detected by the observation of three clearly distinguishable behavioral patterns, was induced.

Formalin having a volume of 20 µl and a concentration of 1% was administered subcutaneously into the dorsal side of the right hind paw of each animal. The specific behavioural changes, such as raising and shaking of the paw, weight loss in the animal and biting and licking reactions, were continuously observed and registered for up to 60 min after the formalin administration. The behavioral changes were weighted differently (a score of 0 to 3) and a pain rate (PR) calculated having the general formula:

$$PR=[(T_0 \times 0)+(T_1 \times 1)+(T_2 \times 2)+(T_3 \times 3)]/180.$$

$T_0$, $T_1$, $T_2$ and $T_3$ each correspond to the time in seconds during which the animal exhibited behavioural pattern 0, 1, 2 or 3. The group contained 10 animals (n=10).

The result of the administration of (1R,2R)-3-(3-dimethylamino-1-ethyl-2-methyl-propyl)-phenol hydrochloride, as well as the result of administrations of combinations of compound no. 2 with the COX-II inhibitors 101, 102, 103 and 104 can be seen from Table 1.

EXAMPLE 4

Randell-Selitto Test

The Randell-Selitto test of Randall and Selitto (Arch. Int. Pharmacodyn., 1957, 111: 409 to 419) is a model for inflammatory pain.

By means of the injection of 0.1 ml 20% baking yeast suspension ventrally into a hind paw an oedema was induced, on which pain was generated 4 hours later by continuously increasing pressure with a stamp (2 mm tip diameter). The measured value to be determined and at the same time also the end point of the pain test was the pressure at which the vocalisation reaction of the animal occurred. The percentage maximum possible effect (% MPE) was calculated. The maximum pressure of the stamp was 250 g. The group size was n=10.

Figure 2:
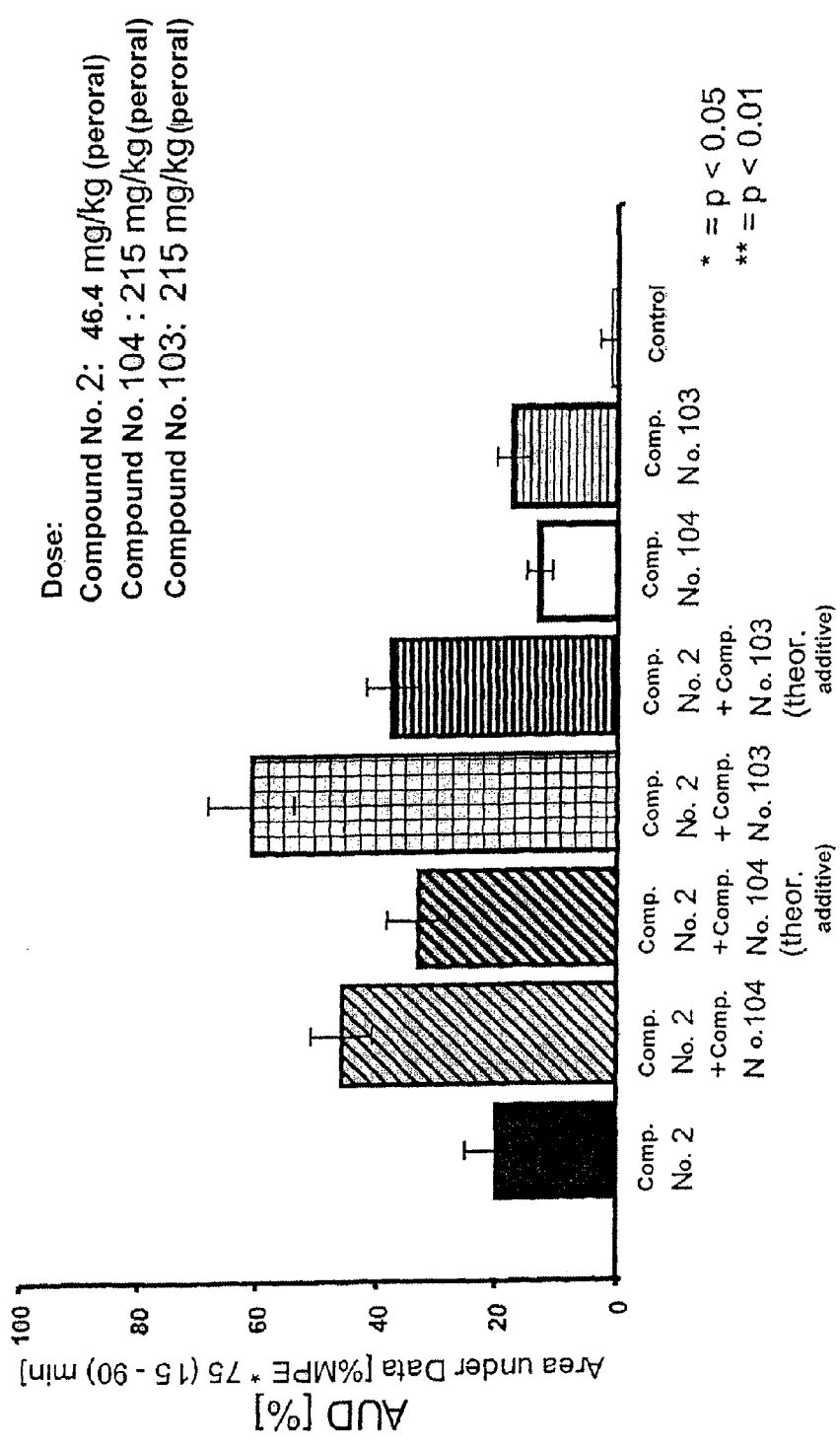

The results of administration of (1R,2R)-3-(3-dimethylamino-1-ethyl-2-methyl-propyl)-phenol, hydrochloride as well as the results of administrations of combinations of compound no. 2 with COX-II inhibitors can be seen from FIGS. 1 to 2 and the following Table 1.

EVALUATION

The selected analgesic, (1R,2R)-3-(3-dimethylamino-1-ethyl-2-methyl-propyl phenol (compound 2), exhibited a moderately strong to strong inhibition of nociception or hyperalgesia in the animal test models.

The theoretical additive value was calculated by adding the mean values from the individual tests of the test substance and COX-II inhibitor. The corresponding standard deviation of the theoretical additive mean value was calculated from the addition of the variances.

In all of the above-listed animal models, the selected 3-(3-dimethylamino-1-ethyl-2-methyl-propyl)-phenol analgesic compound exhibited a moderately strong to strong inhibition of nociception or hyperalgesia. (1R,2R)-3-(3-dimethylamino-1-ethyl-2-methyl-propyl)-phenol showed, in particular, good efficacy in the Randall-Sellito test indicative of usefulness to treat inflammatory pain.

The simultaneous administration of a selective COX-II inhibitor (Rofecoxib or Celecoxib) with compound 2 in the Randall-Selitto test for inflammatory pain resulted in an intensification of effect in comparison to the theoretically calculated purely additive effect. A clear effect-increasing supra-additive effect in the Randall-Selitto test is to be highlighted in the case of the staggered administration of COX-II inhibitor and the selected analgesic (1R,2R)-3-(3-dimethylamino-1-ethyl-2-methyl-propyl)-phenol (compound 2). In these tests, either Rofecoxib or Celecoxib was administered 1 hour prior to the administration of the (1R,2R)-3-(3-dimethylamino-1-ethyl-2-methyl-propyl)-phenol. In a few tests, Rofecoxib was administered as the final preparation Vioxx and Celecoxib as Celebrex.

Results of the tests are summarized in the following table (Table 1). Fixed ratio combination: equieffective dose of the two substances, calculated from the ratio of the respective ED50 values. Fixed dose combination: fixed doses of the respective substances.

TABLE 1

| Test (animal model) | Compound No./ combination (compound A + COX II) | Method of administration | Ratio of compound A (1) to COX-II inhibitor (2) 1: | Ratio of compound A (1) to COX-II inhibitor (2) 2: | Dose of compound A (1) and COX-II inhibitor (2) [mg/kg] 1: | Dose of compound A (1) and COX-II inhibitor (2) [mg/kg] 2: | % effect/ED50 [mg/kg] of compound A | % effect/ED50 [mg/kg] of COX-II inhibitor | % effect/ED50 [mg/kg] of combination (theoretical additive value) | % effect/ED50 [mg/kg] of combination (experimental value) |
|---|---|---|---|---|---|---|---|---|---|---|
| | | | | | Fixed ratio combination | | | | | |
| Writhing (rat) | 2 + 102 | peroral | 1 | 2 | — | — | $ED_{50}$: 33.0 | $ED_{50}$: 60.1 | $ED_{50}$: 47.0 | $ED_{50}$: 23.3 |
| Formalin test (mouse) | 2 + 101 | peroral | 47.3 | 52.7 | — | — | $ED_{50}$: 34.6 | $ED_{50}$: 38.5 | $ED_{50}$: 36.5 | $ED_{50}$: 22.8 |
| Formalin test (rat) | 2 + 101 | peroral | 10.5 | 89.5 | — | — | $ED_{50}$: 18.0 | $ED_{50}$: 154 | $ED_{50}$: 86.0 | $ED_{50}$: 60.6 |
| | | | | | Fixed dose combination: | | | | | |
| Randall-Selitto (rat) | 2 + 104 | peroral | — | — | 31 | 215 | 13.3 | 11.2 | 24.5 | 29.7 |
| Randall-Selitto (rat) | 2 + 101 | peroral | — | — | 31 | 215 | 13.3 | 9.8 | 23.1 | 29.6 |
| | | | | | Fixed dose combination (staggered administration; COX inhibitor 1 hour prior to compound A): | | | | | |
| Randall-Selitto (rat) | 2 + 104 | peroral | — | — | 31 | 215 | 20.0 | 13.0 | 33.0 | 45.7 |
| Randall-Selitto (rat) | 2 + 104 | peroral | — | — | 46 | 215 | 32.6 | 13.0 | 45.6 | 59.8 |

TABLE 1-continued

| Test (animal model) | Compound No./ combination (compound A + COX II) | Method of administration | Ratio of compound A (1) to COX-II inhibitor (2) 1: | 2: | Dose of compound A (1) and COX-II inhibitor (2) [mg/kg] 1: | 2: | % effect/ED50 [mg/kg] of compound A | % effect/ED50 [mg/kg] of COX-II inhibitor | % effect/ED50 [mg/kg] of combination (theoretical additive value) | % effect/ED50 [mg/kg] of combination (experimental value) |
|---|---|---|---|---|---|---|---|---|---|---|
| Randall-Selitto (rat) | 2 + 103 | peroral | — | — | 31 | 215 | 20.0 | 17.3 | 37.3 | 60.9 |
| Randall-Selitto (rat) | 2 + 103 | peroral | — | — | 46 | 215 | 32.6 | 17.3 | 49.9 | 86.1 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

The invention claimed is:

1. A method of treating or inhibiting pain due to inflammation in a patient in need thereof, said method comprising administering to said patient an effective inflammatory pain alleviating amount of a (1R,2R)-3-(3-dimethylamino-1-ethyl-2-methylpropyl)-phenol compound.

2. A method according to claim 1, wherein the compound is present in the form of a physiologically acceptable salt.

3. A method according to claim 2, wherein the physiologically acceptable salt is a hydrochloride salt.

4. A method according to claim 2, wherein the physiologically acceptable salt is a citrate salt.

5. A method according to claim 1, wherein the compound is present in free base form.

6. A method according to claim 1, wherein the compound is present in the form of a pure enantiomer or pure diastereoisomer.

7. A method according to claim 1, wherein said patient is a mammal.

* * * * *